United States Patent [19]

Stogryn et al.

[11] Patent Number: 4,665,195

[45] Date of Patent: * May 12, 1987

[54] PROCESS FOR PREPARING DI-AMINO-POLYALKENYL ETHERS

[75] Inventors: Eugene L. Stogryn, Edison; W.S. Winston Ho, Annandale; Angelo A. Montagna, Summit, all of N.J.

[73] Assignee: Exxon Research and Engineering Company, Florham Park, N.J.

[*] Notice: The portion of the term of this patent subsequent to Dec. 11, 2001 has been disclaimed.

[21] Appl. No.: 565,099

[22] Filed: Dec. 23, 1983

[51] Int. Cl.$^4$ .................... C07C 85/00; C07C 85/02
[52] U.S. Cl. ................... 548/523; 564/480; 564/473; 564/474; 564/447; 564/479
[58] Field of Search ............. 564/480, 473, 479, 474, 564/447; 548/523

[56] References Cited

U.S. PATENT DOCUMENTS

| | | | |
|---|---|---|---|
| 4,409,399 | 10/1983 | Swift et al. | 564/480 |
| 4,487,967 | 12/1984 | Stogryn | 564/474 |
| 4,495,369 | 1/1985 | Werner et al. | 564/480 |

*Primary Examiner*—John Kight
*Assistant Examiner*—M. L. Moore
*Attorney, Agent, or Firm*—Henry E. Naylor

[57] ABSTRACT

Disclosed is a process for producing di-amino-polyalkenyl ethers by reacting (a) one or more acyclic or heterocyclic amino compounds with (b) one or more polyalkenyl ether glycols or polyalkenyl amino ether alcohols, in the presence of a hydrogenation catalyst, at elevated temperatures and pressures.

13 Claims, No Drawings

PROCESS FOR PREPARING DI-AMINO-POLYALKENYL ETHERS

BACKGROUND OF THE INVENTION

1. Field of the Invention

The present invention relates to a process for preparing di-amino-polyalkenyl eithers, including those which are severly sterically hindered by reacting (a) an acyclic primary or secondary amine or a heterocyuclic amino compound with (b) a polyalkenyl either glycol or a polyalkenyl amino either alcohol, in the presence of a hydrogenation catalyst at elevated temperatures and pressures. The resulting di-amino-polyalkenyl eithers are useful in acid gas scrubbing, particularly in the selective removal of $H_2S$ from gaseous streams containing $CO_2$ and $H_2S$.

2. Description of Related Patents and Publications

Recently, it was shown that di-severely sterically hindered amino-polyalkenyl-ethers are superior agents for scrubbing $H_2S$ from gaseous streams containing the same, especially in selectively removing $H_2S$ from normally gaseous mixtures containing $CO_2$ and $H_2S$. Such processes are disclosed in U.S. Pat. Nos. 4,405,482 and 4,405,583, both incorporated herein by reference. The art teaches that these compounds may be prepared by reacting the appropriate primary amine with a bis-(haloalkoxy)alkane or bis-sulfonate ester of a glycolic ether under conditions such that the haloacid or sulfonic acid is eliminated. This process is more fully disclosed in allowed U.S. Ser. No. 339,899 filed Jan. 18, 1982, the disclosure of which is incorporated herein by reference. Disadvantages of such processes include relatively expensive raw materials and product isolation. That is, the initially formed product is an amine salt which requires caustic treatment as a part of the product isolation procedure.

Consequently, there exists a need in the art for methods of preparing di-severely sterically hindered amino-polyalkenyl ethers which would not be limited by such disadvantages.

SUMMARY OF THE INVENTION

In accordance with the present invention there is provided a process for preparing di-amino-polyalkenyl ethers by use of relatively low cost polyalkenyl ether glycols and polyalkenyl amino ether alcohols, which avoids the neutraliztion step required by the aforementioned prior art method, thereby circumventing the formation of inorganic salts as well as the problems associated with salt disposal.

The process of the present invention comprises reacting:

(a) one or more acyclic cyclic amino compounds represented by the general formulas:

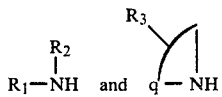

where $R_1$ and $R_2$ are independently selected from the group consisting of primary, secondary and tertiary alkyl radicals having 1 to 8 carbon atoms and cycloalkyl radicals having 3 to 8 carbon atoms with the proviso that at least one of $R_1$ and $R_2$ is a secondary or tertiary alkyl radical, and hydrogen wherein only one of $R_1$ and $R_2$ can be hydrogen, q represents the number of carbon atoms in the heterocyclic ring and is a positive integer ranging from 2 to 10, and $R_3$, which is optional, is selected from the group consisting of alkyl and cycloalkyl radicals and which may be substitutents of one or more of the carbons of the ring; with (b) one or more polyalkenyl either glycols or polyalkenyl aminoether alcohols represented by the general formula:

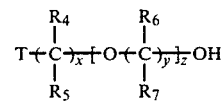

where T is a hydroxyl group or an amino group as set forth in (a) above, $R_4$, $R_5$, $R_6$ and $R_7$ are each independently selected from the group consisting of hydrogen, $C_1$ to $C_4$ alkyl radicals, and $C_3$ to $C_8$ cycloalkyl radicals with the proviso that if only one of $R_1$ and $R_2$ directly attached to the nitrogen atom is a secondary alkyl radical and neither of them is a tertiary alkyl radical, at least one of $R_4$ and $R_5$, or at least one of $R_6$ and $R_7$ directly bonded to the carbon which is bonded to the hydroxyl group, is an alkyl or cycloalkyl radical, x and y are each positive integers independently ranging from 2 and 4, and z is a positive integer ranging from 1 to 10 with the proviso that when T is a hydroxyl group and z is 1, the amino compound reactant in (a) above is a heterocyclic amine or the sum of x and y is from 5 to 8, or when T is an acyclic secondary amino group and z is 1, the sum of x and y is from 5 to 8, said process being carried out in the presence of a catalytically effective amount of a supported Group VIII metal containing hydrogenation catalyst at elevated temperatures and pressures and wherein the mole ratio of amino compound to polyalkenyl compound is at least 2 to 1 when T is hydroxyl and is at least 1 to 1 when T is an amino group.

Preferably, $R_1$ is an alkyl radical having 4 to 6 carbon atoms, $R_2$, $R_3$, $R_4$, $R_5$, $R_6$, and $R_7$ are hydrogen and x and y are 2. Most preferably the amino compound is tertiarybutylamine, x and y are 2, and z is 2 or greater.

DETAILED DESCRIPTION OF THE INVENTION

Both primary and secondary acyclic and cyclic amino compounds may be used in the practice of the present invention. When an acyclic amino compound is used it will conform to the general formula:

where $R_1$ and $R_2$ are independently selected from the group consisting of primary, secondary and tertiary alkyl radicals having 1 to 8 carbon atoms and cycloalkyl radicals having 3 to 8 carbon atoms with the proviso that at least one of $R_1$ and $R_2$ is a secondary or tertiary alkyl radical, and hydrogen wherein only one of $R_1$ and $R_2$ can be hydrogen. When a cyclic (heterocyclic) amino compound is used herein, it will conform to the general formula:

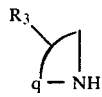

where q is the number of carbons in the ring and ranges from 2 to 10, and $R_3$ which is optional is selected from the group consisting of alkyl and cycloalkyl radicals which are pendant to one or more of the carbons of the ring. The heterocyclic ring may be saturated or unsaturated. Preferred is when it is saturated and contains 3 to 6 carbon atoms, more prefered is when the ring is saturated and contains 4 to 5 carbon atoms, most preferred is when the ring is a 4 carbon saturated ring.

Preferred are the acyclic amino compounds, most preferred is tertiarybutylamine (TBA).

Both polyalkenyl ether glycols and polyalkenyl aminoether alcohols may be reacted with the amino compounds hereof to produce di-amino polyalkenyl ethers in accordance with the present invention. Polyalkenyl ether glycols suitable for use herein are those represented by the general formula:

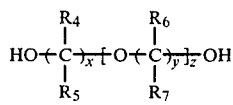

Wherein $R_4$, $R_5$, $R_6$, and $R_7$ are each independently selected from the group consisting of hydrogen, $C_1$ to $C_4$ alkyl radicals, and $C_3$-$C_8$ cycloalkyl radicals with the proviso that if only one of $R_1$ and $R_2$ directly attached to the nitrogen atom of the acyclic amino compound is a secondary alkyl radical and neither of them is a tertiary alkyl radical, at least one of $R_4$ and $R_5$, or at least one of $R_6$ and $R_7$ directly bonded to the carbon which is bonded to the hydroxyl group, is an alkyl or cycloalkyl radical, x and y are each positive integers independently ranging from 2 to 4, and z is a positive integer ranging from 1 to 10, with the proviso that if z is 1, the amino compound reactant in (a) is a heterocyclic amine, or the sum of x and y is from 5 to 8. Preferred is when $R_4$, $R_5$, $R_6$ and $R_7$ are hydrogen, x and y are 2, and z is 2 or greater.

Polyalkenyl aminoether alcohols suitable for use herein are those wherein the amino group is cyclic or heterocyclic. Those containing an acyclic amino group are represented by the general formula:

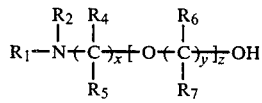

Where $R_1$ and $R_2$ are the same as those set forth above for the acyclic amino compounds, $R_4$, $R_5$, $R_6$, $R_7$, x, and y are the same as those set forth above for the polyalkenyl ether glycols, and Z is a positive integer ranging from 1 to 10, with the proviso that when one of $R_1$ and $R_2$ is hydrogen and Z is 1, the sum of x and y is from 5 to 8. Polyalkenyl aminoether alcohols containing a heterocyclic amino group are represented by the general formula:

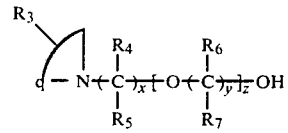

where $R_3$ and q are the same as those set forth above for the heterocyclic amino compounds, and $R_4$, $R_5$, $R_6$, $R_7$, x and y are the same as those set forth above for the polyalkenyl ether glycols, and z is from 1 to 10.

It is understood that by the practice of the present invention, one of the amino groups may be acyclic and the other heterocyclic, both may be acyclic, or both may be heterocyclic. It is preferred when both are tertiarybutyl.

The diamination process hereof is carried out under pressure at a temperature ranging from about 160° to about 425° C., preferably from about 180° to about 400° C., and most preferably from about 190° to about 350° C. The pressures in the reactor may range from about 50 to about 3000 psig, preferably from about 100 to about 1000 psig, and most preferably from about 150 to about 750 psig.

The reactor used may include any suitable vessel capable of withstanding the pressures necessary to carry out the amination process. Preferably, the amination process is carried out in a fixed bed reactor whereby the reactants are passed over a fixed bed of the catalyst, either concurrently or countercurrently. Other reactors suitable for use herein include moving be reactors and continuous stirred reactors. For example, in a continuous stirred reactor the catalyst is circulated and the reactants and reaction product are passed through the reaction vessel at a controlled rate.

The hydrogenation catalyst used in the amination process herein may include any of the known hydrogenation catalysts. Illustrative hydrogenation catalysts include platinum, palladium and other noble metals such as ruthenium, rhodium, osmium and iridium deposited on inert supports such as carbon, silica, alumina or other refractory oxides, Raney nickel, nickel-on-kieselguhr, nickel on inert support, massive nickel or nickel-cobalt or nickel-cobalt-copper coprecipitated with silicate and/or aluminum salts having alumina or kieselguhr supports. Preferred catalysts include coprecipitated nickel, nickel-cobalt, and nickel-cobalt-copper supported on silica, alumina or a mixture thereof. Also preferred is platinum supported on alumina. Still more preferred are catalysts having increasing concentrations of nickel, about 40% to 70% nickel, by weight. Since preferred catalysts include those massive-metal coprecipitated hydrogentation catalysts described in U.S. Pat. Nos. 3,697,445; 4,251,394; 4,251,672; 4,263,173; 4,263,225; 4,273,680; 4,273,939; 4,307,248; 4,318,829; and the metal coprecipitated catalysts containing aluminum and silica disclosed and claimed in U.S. Ser. Nos. 388,966 and 388,967, the disclosures of which are incorporated herein by reference. It is preferred that the catalyst be reduced or activated by a reductant, such as hydrogen prior to use in the amination reaction. This reduction or activation is typically carried out by passing hydrogen over the catalyst at temperatures ranging from 175° to about 400° C., preferably 200° to about 350° C.

The concentration of the hydrogenation catalyst is that which is catalytically effective and that amount will generally range from about 0.1 to about 10 weight percent, preferably from about 2 to about 8 weight percent, based on the weight of the reactant charge. The normal pretreatment conditions and handling of the hydrogenation catalyst should be practiced as known to those skilled in the hydrogenation catalyst art.

The mole ratio of amino compound to polyalkenyl ether glycol employed herein must be at least 2:1. Generally for economical reasons not more than a 6:1 ratio will be used. If less than two moles of amino compound per mole of the glycol is used then a mono-aminoether alcohol will be produced as opposed to the di-amino-polyalkenyl ether. If the amino compound is reacted with a polyalkenyl aminoether alcohol it is preferred that the mole ratio of amino compound to alcohol be greater than 1:1 to speed the reaction.

For purposes of this invention it may be desirable to include a inert solvent in the reaction medium. Preferably the solvent is a solvent such as cyclic or linear ether or a hydrocarbon containing compound in which the reactants will dissolve. The solvent should be of relatively low molecular weight to facilitate its removal from the product of the reaction. The amount of the solvent may vary, but will generally range from about 10 to 50 wt. %, preferably from 15 to 30 wt. %, based on the weight of the reactants used. Preferred solvents include tetrahydrofuran, dimethylether of ethylene glycol, and toluene.

Reduction of the catalyst may be carried out in situ while conducting the process by the presence of hydrogen. Hydrogen, however, is not essential to conducting the process but is preferably employed, for example, to minimize catalyst deactivation.

Once the reaction has been completed, the reaction product can be conveniently recovered by known techniques such as solvent evaporation, distillation and the like.

The invention is illustrated further by the following examples which, however, are not to be taken as limiting in any respect. All parts and percentages, unless expressly stated otherwise, are by weight.

Example 1

To a 300 ml stainless steel, stirred autoclave there was added 21 g of tertiarybutylamine, 20 g of tertiarybutylaminoethoxyethoxyethanol, 0.6 g of Ni-Al$_2$O$_3$-SiO$_2$ catalyst (Harshaw NI-5132P), and 50 ml of toluene. The autoclave containing the reactants was heated to 200° C. under autogenous pressure (180 psi) for 6 hours. The contents were cooled, removed and filtered. The autoclave and filtercake were washed with additional toluene. G.C. analysis revealed that the product was comprised of about 91 wt. % 1,2-bis-(tertiarybutylaminoethoxy) ethane and less than about 5 wt. % tertiarybutylaminoethoxyethoxyethanol. Vacuum distillation gave 17.3 g of 1,2-bis-(tertiarybutylaminoethoxy) ethane, having a boiling point of 125°–128° C./3 mm.

Example 2

Following the same procedure as in Example 1 above, 38.9 g tertiarybutylamine, 20 g of triethylene glycol, 1 g of Ni-Al$_2$O$_3$SiO$_2$ catalyst (Harshaw Ni-5132P), and 50 ml of toluene were heated at 200° C. in an autoclave at autogeneous pressure (160 psi). After four hours at 200° C., conversion of triethylene glycol was complete, as evidenced by G.C. analysis. The product composition was analyzed and was found to be comprised of 16.1 wt. % of tertiarybutylaminoethoxyethoxyethanol and 76.6 wt. % 1,2-bis-(tertiarybutylaminoethoxy)ethane.

Example 3 (Comparative)

Following the same procedure as in Example 1, 20 g of tertiarybutylaminoethoxyethanol (TBEE) 27.2 g of tertiarybutylamine (TBA) 6 g of 1% Pt/graphite catalyst (Alfa), and 50 ml of toluene were stirred together in an autoclave at autogeneous pressure at 200° C. for 22 hours. The resulting product was analyzed by G.C. and it was found that the concentration of TBEE had dropped to 51.4 wt. % and that 35.7 wt. % of N-tertiarybutylmorpholine was present. No diaminated product was found. This example demonstrates that relatively a large molar excess of TBA will not produce the expected corresponding diamine product but that intramolecular amination of the TBEE terminal hydroxyl group occurs instead.

Example 4 (Comparative)

Following the same procedure as the above examples 25 g of TBEE, 17 g of TBA, 50 ml of toluene, and 0.5 g of Ni-Al$_2$O$_3$-SiO$_2$ catalyst (Harshaw Ni-5132P) were stirred in an autoclave at 200° C. at autogeneous pressure for 22 hours. The resulting product was analyzed and was found to be comprised of 18.9 wt. % N-tertiarybutylmorpholine, 45 wt. % TBEE, and decomposition.

What is claimed is:

1. A process for producing a di-amino polyalkenyl ethers comprising reacting:

(a) one or more acyclic or heterocyclic amino compounds represented by the general formulas:

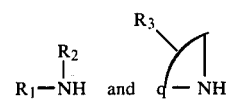

where $R_1$ and $R_2$ are independently selected from the group consisting of primary, secondary and tertiary alkyl radicals having 1 to 8 carbon atoms and cycloalkyl radicals having 3 to 8 carbon atoms with the proviso that at least one of $R_1$ and $R_2$ is a secondary or tertiary alkyl radical, and hydrogen wherein only one or $R_1$ or $R_2$ can be hydrogen, q is the number of carbon atoms in the heterocyclic ring and is a positive integer ranging from 2 to 10, and $R_3$, which is optional, is selected from the group consisting of alkyl and cycloalkyl radicals and which may be pendant to one or more of the carbons in the ring; and (b) a polyalkenyl ether glycol or a polyalkenyl amino ether alcohol having the general formula:

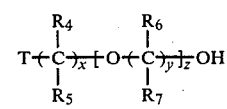

where $R_4$, $R_5$, $R_6$, and $R_7$ are each independently selected from the group consisting of hydrogen, $C_1$ to $C_4$ alkyl radicals, and $C_3$ to $C_8$ cycloalkyl radicals, with the proviso that if only one of $R_1$ and $R_2$ directly attached to the nitrogen atom is a secondary alkyl radical and neither of them is a tertiary alkyl radical, at least one of $R_4$ and $R_5$, or at lest one of $R_6$ and $R_7$ directly bonded to the carbon which is bonded to the hydroxyl group, is an alkyl or cycloalkyl radical, x and y are each positive integers idependently ranging from 2 to 4, and z is a positive integer ranging from 1 to 10 when T is a heterocyclic amino group, when T is a hydroxyl group with the proviso that when z is 1, the amino compound reactant in (a) is a heterocyclic amine or the sum of x and y is from 5 to 8, or when T is acyclic secondary amino group with the proviso that when z is 1, the sum of x and y is from 5 to 8, said process being carried out in the presence of a catalytically effective amount of supported Group VIII metal containing hydrogenation catalyst at elevated temperatures and pressures and wherein the mole ratio of amino compound to polyalkenyl ether glycol is at least 2:1 when T is hydroxyl and is at least 1:1 when T is an amino group.

2. The process of claim 1 wherein the amino compound is acyclic wherein $R_1$ is a tertiary alkyl radical having 4 to 6 carbon atoms and $R_2$ is hydrogen, $R_4$, $R_5$, $R_6$ and $R_7$ are hydrogen, x, y and z are 2, and T is a hydroxyl group.

3. The process of claim 2 wherein $R_1$ is tertiary butyl.

4. The process of claim 1 wherein the amino compound is a heterocyclic compound having 3 to 6 carbons in a saturated ring, $R_4$, $R_5$, $R_6$ and $R_7$ hydrogen, x, y and z are 2, and T is a hydroxyl group.

5. The process of claim 4 wherein the heterocyclic compound is pyrrolidine.

6. The process of claim 1 wherein the reaction is carried out at a temperature ranging from about 160° C. to about 425° C. and at a pressure ranging from about 50 to about 3000 psig.

7. The process of claim 6 wherein the reaction is carried out at a temperature ranging from about 180° C. to about 400° C. and at a pressure ranging from about 100 to about 1000 psig.

8. The process of claim 7 wherein the reaction is carried out at a temperature ranging from about 190° C. to about 350° C. and at a pressure ranging from about 150 psig to about 750 psig.

9. The process of claim 3 wherein the reaction is carried out at a temperature ranging from about 190° C. to about 350° C. and at a pressure ranging from about 150 psig to about 750 psig.

10. The process of claim 5 wherein the reaction is carried out at a temperature ranging from about 190° C. to about 350° C. and at a pressure ranging from about 150 to about 750 psig.

11. The process of claim 1 wherein the hydrogenation catalyst is a nickel, a cobalt, a nickel-cobalt-copper, or a platinum catalyst all of which are supported on alumina, silica, or alumina-silica.

12. The process of claim 9 wherein the hydrogenation catalyst is a nickel, a cobalt, a nickel-cobalt-copper, or a platinum catalyst all of which are supported on alumina, silica, or alumina-silica.

13. The process of claim 10 wherein the hydrogenation catalyst is a nickel, a cobalt, a nickel-cobalt-copper, or a platinum catalyst all of which are supported on alumina, silica, or alumina-silica.

* * * * *